United States Patent [19]

Drake et al.

[11] 4,288,625
[45] Sep. 8, 1981

[54] DINITRILES, DIAMINES, AND POLYAMIDES

[75] Inventors: Charles A. Drake; Stanley D. Turk, both of Bartlesville, Okla.

[73] Assignee: Phillips Petroleum Co., Bartlesville, Okla.

[21] Appl. No.: 716,406

[22] Filed: Aug. 23, 1976

Related U.S. Application Data

[63] Continuation of Ser. No. 499,660, Aug. 22, 1974, abandoned.

[51] Int. Cl.$^3$ .............................................. C07C 85/12
[52] U.S. Cl. ............................... 564/372; 260/465 H; 260/465.8 R; 564/152; 564/153; 564/375; 564/460; 564/461; 564/491; 564/512
[58] Field of Search .................... 260/583 P, 570.5 P, 260/563 R

[56] References Cited

U.S. PATENT DOCUMENTS

| | | | |
|---|---|---|---|
| 2,752,328 | 6/1956 | Magat | 260/78 |
| 2,864,807 | 12/1958 | Nobis et al. | 260/78 |
| 2,891,088 | 6/1959 | Condo et al. | 260/465 |
| 3,117,162 | 1/1964 | Rylander et al. | 260/570.9 X |
| 3,361,821 | 1/1966 | Wallis et al. | 260/583 |
| 3,412,156 | 11/1968 | Ueda et al. | 260/583 |
| 3,418,375 | 12/1968 | Schmitt et al. | 260/583 |
| 3,575,935 | 4/1971 | Elam | 260/78 |
| 3,580,949 | 5/1971 | Gruenman et al. | 260/570.5 |
| 3,632,625 | 1/1972 | Funten et al. | 260/464 |
| 3,673,251 | 6/1972 | Frampton et al. | 260/570.5 X |

FOREIGN PATENT DOCUMENTS 619706  3/1949  United Kingdom ............... 260/583

OTHER PUBLICATIONS

Overberger et al., "Journ. Amer. Chem. Soc.", vol. 81, pp. 4697-4701 (1959).

*Primary Examiner*—Robert V. Hines

[57] ABSTRACT

Unsaturated dinitriles are reacted with an aromatic compound such as benzene in the presence of a Lewis acid such as aluminum chloride to yield novel aralkylenedinitriles, such as 5-methyl-5-phenylnonanedinitrile and isomers thereof. The aralkylenedinitriles can be reduced to novel aralkylenediamines or novel cycloalkylalkylenediamines. Polymerization of the aralkylenediamines or cycloalkylalkylenediamines with polycarboxylic acids provides novel polyamides of tough, clear, colorless character.

21 Claims, No Drawings

DINITRILES, DIAMINES, AND POLYAMIDES

This is a continuaion of application Ser. No. 499,660 filed Aug. 22, 1974, now abandoned.

FIELD OF THE INVENTION

The invention relates to novel dinitriles and their preparation. In another aspect, the invention relates to novel diamines and their preparation. In a further aspect, the invention relates to novel polyamides and their preparation.

BACKGROUND OF THE INVENTION

Synthetic polymers of the polyamide type have been prepared by polymerizing a variety of diamines with a variety of dicarboxylic acids. The search for new polyamide precursors continues in order to provide polymeric products such as fibers and molding resins with ever more desirable properties.

OBJECTS OF THE INVENTION

It is an object of the invention to produce novel polyamide precursors. Another object of the invention is to provide novel dinitriles. A further object of the invention is to provide novel diamines. A still further object of the invention is to provide novel polyamide compositions.

Other aspects, objects, and advantages of the invention will be apparent from a study of the disclosure including the appended claims.

SUMMARY OF THE INVENTION

Unsaturated dinitriles are reacted with an aromatic compound, such as benzene, in the presence of a Lewis acid, such as aluminum chloride, to yield novel aralkylenedinitriles such as 5-methyl-5-phenylnonanedinitrile and isomers thereof.

Reduction of these novel aralkylenedinitriles produces novel aralkylenediamines such as 5-methyl-5-aryl-1,9-nonanediamine, and cycloalkylalkylene diamines such as 5-methyl-5-cycloalkyl-1,9-nonanediamine. These new diamines, both the aralkylene type, and the cycloalkylalkylene type, are desirable products for use in polymerization such a condensation polymerization, such as reaction with a polycarboxylic acid such as terephthalic acid to yield desirable polyamides of tough, clear, colorless polymeric character.

ARALKYLENEDINITRILES

In accordance with one aspect of our invention, at least one unsaturated dinitrile and at least one aromatic compound are reacted in the presence of a Lewis acid to produce novel aralkylenedinitriles. The novel aralkylenedinitriles can be represented by the general formulae

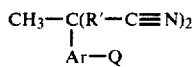  (I)

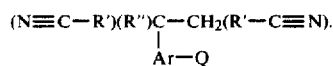  (II)

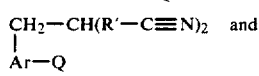  (III)

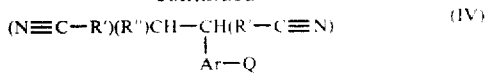  (IV)

The isomeric aralkylene dinitriles represented by (III) and (IV) are usually produced in relatively small amounts as compared to types (I) and/or (II).

Ar represents a divalent hydrocarbyl radical derived from the aromatic compound H—Ar—Q and Q represents hydrogen or other substituent on H—Ar—. If Q is hydrogen, —Ar—Q is an aryl radical and when Q is other than hydrogen, —Ar—Q is a substituted aryl radical. Preferably preferred is —Ar—Q which is phenyl, e.g., H—Ar—Q is benzene.

UNSATURATED DINITRILES

Unsaturated dinitriles, prepared by such as the reaction of a monoolefin and an alpha, beta-unsaturated mononitrile, or by other known methods such as halide displacement with the cyano group, can be represented by the general formulae:

  (V)

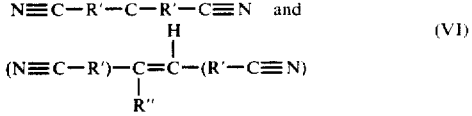  (VI)

in which each R' represents a linear or branched alkylene or alkylidene radical of at least one carbon atom, with one valence attached to the cyano group as indicated by the formulae. R" is a linear or branched alkyl radical of at least one carbon atom. R' and R" are not limited by carbon number as far as our invention is concerned, though presently we prefer R' to contain up to 20 carbon atoms, R" up to 10 carbon atoms, such that the dinitriles, contain 9 to 30 carbon atoms, more preferably 9 to 16 carbon atoms, per molecule, since the ultimately prepared diamines are more reactive in preparing the ultimately desired polyamides.

Among the dinitriles according to the formulae given to represent the dinitriles which we use as starting materials in our invention, are dinitriles such as 5-methylenenonanedinitrile; 5-methyl-4-nonenedinitrile; 2-methyl-4-methyleneoctanedinitrile; 2,4-dimethyl-4-octenedinitrile; 2,4-dimethyl-3-octenedinitrile; 2,6-dimethyl-4-methyleneheptanedinitrile; 2,4,6-trimethyl-3-heptenedinitrile; 3-neopentylidenenonanedinitrile; 5-neopentyl-5-nonenedinitrile; and the like. Mixtures of two or more dinitriles can be employed if desired in our invention. In production of the dinitriles by reaction of a mono-1-olefin with an unsaturated mononitrile, the product usually is a mixture of the unsaturated isomeric dinitriles. The ratio of V to VI obtained in the preparation of diadduct from the unsaturated mononitrile and mono-1-olefin varies with the particular monomers, but in the case of the presently preferred acrylonitrile and isobutylene, the ratio obtained is about 60/40. Thus, the ratio of (I+III)/(II+IV) would be about 60/40, and the ratio of I/II would be about 60/40.

AROMATIC COMPOUNDS

The aromatic compounds include benzene, also napththalene, and further, their substituted compounds which can be represented by the general formula H—Ar—Q in which Ar represents the phenylene or naphthalene radical, preferably phenyl, and Q represents —H, —X, —R''', —N(R''')$_2$, —NH$_2$.HX, —OR''', —SH, —OH, or —SR''', preferably —H. X is a halogen and can be fluorine, chlorine, bromine or iodine. R''' is an alkyl radical having 1 to 6 carbon atoms. Specific examples of suitable compounds include benzene, naphthalene, toluene, chlorobenzene, N,N-dimethylaniline, aniline hydrochloride, anisole, benzenethiol, 1-chloronaphthalene, phenol, methylphenyl sulfide, 2-methoxynaphthalene, and the like, preferably of 6 to 20 carbon atoms per molecule. The above compounds and many others which fit the general formula H—Ar—Q are well known in the art.

Among suitable Lewis acid compounds, able to act as catalysts, which coordinate with an electron pair, usually by virtue of having a less than a full octet of electrons on an atom in the compound, are such as AlCl$_3$, BF$_3$, FeCl$_3$, ZnCl$_2$, SnCl$_4$, HF, HgCl$_2$, SbCl$_5$, and the like.

The reaction of the unsaturated dinitrile with the aromatic compound in the presence of a Lewis acid catalyst often is desirably and conveniently carried out in the presence of an excess of the aromatic compound which thus serves as reaction diluent. The reaction optionally can be carried out utilizing added diluent, such as nitrobenzene, benzotrifluoride or 1,1,2,2-tetrachloroethane inert in the reaction environment. In any event, it is preferred that the molar ratio of aromatic compound to dinitrile be at least about 1:1 for suitable yields.

The amount of Lewis acid catalyst employed depends to some extent on the nature of the reactants, since it is recognized that certain groups, e.g., the —C≡N group, tend to complex with a molar equivalent of catalysts such as AlCl$_3$. Thus if no other complexing group or groups are present in the reactants other than the —C≡N group, the amount of catalyst preferably should be in the range of at least a slight molar excess, e.g., about 1.05:1 up to about a 2:1 molar ratio of catalyst per —C≡N group in the dinitrile reactant. If other complexing groups are present in the aromatic compound reactant, suitable allowance should be made for such groups such that, in any event, a molar excess of catalyst to complexting groups is present in the reaction mixture.

The temperature employed can vary over a wide range. Presently, we suggest that a range of about 25° up to the boiling point of the diluent and/or aromatic compund reactant, preferably about 60° to 100° C. The reaction time also can vary considerably, with satisfactory reaction being obtained in the range of a few minutes such as about 15 minutes up to 3 hours or more, preferably up to about 1.5 hours. Pressures employed are not believed to be critical, and for convenience can be at or near atmospheric pressure, though higher pressures can be employed, if desired, to maintain reactants substantially in the liquid phase.

The charge order of the catalyst, reactants and diluent, where used, is not believed to be critical. However, it is presently preferred to add the Lewis acid to a solution of the aromatic compound and unsaturated dinitrile in diluent, where used. If an added inert diluent is not employed, the catalyst can be added to a mixture of unsaturated dinitrile and aromatic reactant.

At the conclusion of the desired reaction interval, the reaction mixture can be subjected to any suitable product recovery means and steps, such as hydrolysis of the mixture to destroy the catalyst, extraction of the mixture with an organic solvent for the product, drying of the extracted material and solvent, removal of the organic solvent, and fractional distillation of the crude product.

ARALKYLENEDIAMINES

The aralkylenedinitrile reaction product of the unsaturated dinitrile with the aromatic compound in the presence of Lewis acid catalysts can be hydrogenated to reduce the —C≡N groups to amino groups —CH$_2$NH$_2$. The resulting novel aralkylenediamine compounds can be represented by:

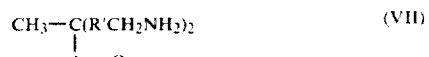   (VII)

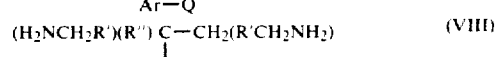   (VIII)

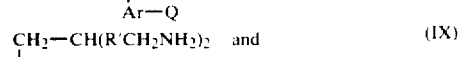   and   (IX)

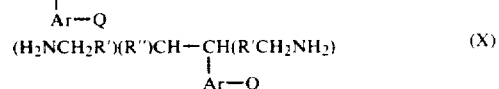   (X)

Of course, minor amounts of the isomeric diamines represented by IX and X also are produced if the corresponding isomeric dinitriles are present.

The hydrogenation of the aralkylenedinitriles to aralkylenediamines can be carried out under hydrogenation conditions such as employing a Raney nickel or Raney cobalt or other supported nickel or cobalt catalyst. Ruthenium-based catalyst also are available, such as ruthenium oxide or ruthenium oxide-on-alumina or on other suitable support materials. Rhodium-based catalysts also can be employed, such as rhodium-on-alumina, or on carbon, or on other support materials. A diluent can be employed during this reaction but not necessary.

The catalyst levels employed are those sufficient to hydrogenate the amount of dinitrile present, and an exemplary amount would be about 0.1 to 50 percent by weight of catalyst expressed in terms of the metal, e.g., Co, Ni, Ru or Rh component excluding support, if any, based on the weight of aralkylene dinitrile charged to the reaction mixture and presently preferred is a concentration of catalyst of about 0.3 to 20 percent by weight on this basis. Since there is no stoichiometry between the hydrogenation catalyst and the unsaturated dinitrile, it seems simpler and more easily understood to base it simply on the total dinitrile weight.

Presently preferred hydrogenation conditions include hydrogenation employing any of the above catalysts or mixtures thereof under elevated pressures such as about 500 to 5000 psig, presently preferred, because the reaction is more easily controlled, are pressures of about 1000 to 3000 psig hydrogen pressure, employing hydrogenation times necessary for the extent of reaction desired, generally in the range of such as 0.25 to 5 hours, presently preferred because of economy and efficiency about 1 to three hours.

Hydrogenation conditions include the presence of ammonia sufficient to repress undesirable side reactions leading to secondary and/or tertiary amines. The amount of ammonia employed should be at least one mol per mol of CN group in the dinitrile, and can conveniently range from such as 1 to 20, preferably because of efficiency and ease of handling, 7-13 mols of ammonia per mol of CN group in the dinitrile. If desired, reaction inert reaction hydrocarbons or reaction inert ethers can be used in any convenient amounts.

Hydrogenation temperature conditions are those known in the art for reduction of —CN groups with the types of catalysts employed, and any suitable temperature pressure relationship can be utilized according to the catalyst. For ruthenium-based catalysts, the temperature generally can be about 100° to 250° C., preferably because of ease of control, about 120° to 170° C. For rhodium-based catalysts, a suitable hydrogenation temperature can be generally about 25° to 150° C., preferably because of ease of control, about 50° to 100° C. For cobalt-based catalyst or nickel-based catalyst, including the Raney type catalyst, temperatures in the range of about 70° to 200° C. are considered suitable, preferably because of ease of control about 100° to 150° C. can be utilized.

The novel aralkylenediamines so prepared can be recovered from the hydrogenation reaction by filtration of the hydrogenation reaction mixture followed by frictional distillation, other recovery modes can be utilized as can be convenient, as known to those skilled in the arts.

CYCLOALKYLALKYLENEDIAMINES FROM ARALKYLENEDIAMINES

While the novel aralkylenediamines can be employed as such in the preparation of our novel polyamides, the aralkylenediamines can be further reduced to novel cycloalkylalkylenediamines, if desired, such as by further reduction by a second hydrogenation step.

The resulting novel cycloalkylalkylenediamines can be represented by:

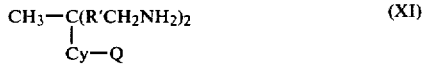
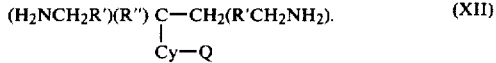
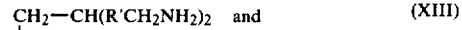
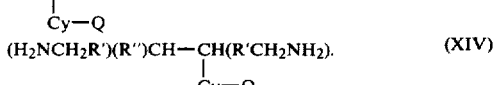

$$CH_3-C(R'CH_2NH_2)_2 \atop Cy-Q \qquad (XI)$$

$$(H_2NCH_2R')(R'') C-CH_2(R'CH_2NH_2). \atop Cy-Q \qquad (XII)$$

$$CH_2-CH(R'CH_2NH_2)_2 \text{ and} \atop Cy-Q \qquad (XIII)$$

$$(H_2NCH_2R')(R'')CH-CH(R'CH_2NH_2). \atop Cy-Q \qquad (XIV)$$

The isomeric diamines represented by XIII and XIV are produced, usually in minor amounts, if the corresponding isomeric dinitriles were present in the original mixture of reaction product of unsaturated dinitrile with aromatic compound when reacted in the presence of the Lewis acid catalyst.

Cy represents the divalent hydrocarbyl radical derived from complete hydrogenation of the aromatic radical as previously described, and Q represents hydrogen or the previously described substituent on the now saturated ring Cy. If Q is hydrogen, then —Cy—Q represents a cycloalkyl radical, and when Q is other than hydrogen, then —Cy—Q represents a substituted cycloalkyl radical.

For reduction of the aralkylenediamines to cycloalkylalkylenediamines, any suitable hydrogenation catalyst can be employed that will affect the reduction of hydrogenation of a benzene or naphthalene type ring. For this purpose, platinum-based catalysts are particularly suitable, and such catalysts include platinum oxide, $PtO_2$, as well as platinum metal or hydrogen-reducible compounds of platinum on suitable support materials such as carbon, aluminas and the like. Such platinum-based hydrogenation catalysts are well known in the art. Any other mode or means of reduction of the benzene or naphthalene ring known in the arts can be utilized.

Hydrogenation conditions utilized can be those known in the arts suitable for reduction of the types of rings involved. Exemplary hydrogenation over platinum-based catalysts generally can be carried out at temperatures of about 25° to 150° C., preferably because of ease of control and suitable reaction rates, about 50° to 100° C. Hydrogen pressures of about 0–200 psig, preferably because of ease of control and efficiency about 30–100 psig, can be employed. Catalysts level employed are those suitable and effective for the catalysts under the conditions of temperature and pressure. As an exemplary amount, 0.1–10 percent by weight based on the amount of aralkylenediamine charged the reaction mixture, preferably because of economy and efficiency about 1–5 weight percent. Contact in time can be as necessary for the reduction of the compounds involved, and typically times of about 0.25 to 5 hours should be suitable, preferably because of efficiency about 1–3 hours.

Hydrogenation conditions utilized preferably include the reduction of the aralkylenediamine in the presence of a diluent. Suitable diluents for hydrogenation using platinum-based catalysts include the normally liquid organic carboxylic acids such as acetic acid, propionic acid, and the like. The amount of diluent employed generally should be at least equivalent to the molar amount of the amine being hydrogenated, and preferably because of ease in handling will be in excess of this, though the upper limit is merely a matter of choice based on economy and efficiency of operation and ease of handling the reaction mixture.

After reduction of the aralkylenediamine to the corresponding cycloalkylalkylenediamine, the resulting cycloalkylalkylenediamines can be recovered from the reaction mixture by any convenient method for recovery known in the arts. Suitable modes include stripping of excess diluent, neutralizing of remaining organic carboxylic acid diluent, extracting the liberated diamine with a suitable solvent such as benzene, diethyl ether or the like, followed by fractional distillation for recovery of the diamine product. Other suitable methods of course can be employed as a matter of choice.

The term "polyamine" as used herein describes those compounds which contain at least two —NH2 groups per molecule prepared as described, and preferably will be a diamine.

CYCLOALKYLALKYLENEDIAMINES FROM ARALKYLENEDINITRILES

In another aspect of our invention, the novel aralkylenedinitriles described hereinabove, can be directly hydrogenated in a substantially one-step operation directly to the above-described cycloalkylalkylenediamines.

The catalysts considered to be suitable for employment in the catalytic hydrogenation process according to this aspect of our invention comprise a combination of a palladium catalyst component (A) and a ruthenium or rhodium or both component (B).

The palladium catalyst component (A) can be in the form of finely divided palladium metal or compounds of palladium reducible by hydrogen to palladium metal.

The palladium catalyst component can also be in the form of palladium metal deposited on a suitable support or in the form of hydrogen reducible compounds of palladium dispersed on a suitable support. The (B) component can be finely divided elemental ruthenium or rhodium, compounds of ruthenium or rhodium reducible to finely divided elemental ruthenium or rhodium by hydrogen, ruthenium or rhodium metal on a suitable support or hydrogen reducible compounds of ruthenium or rhodium on a suitable support.

Among the compounds of palladium and of ruthenium or of rhodium reducible by hydrogen to finely divided elemental catalyst component include the oxides, halides, nitrates, sulfates, oxalates, acetates, carbonates, propionates, tartrates, hydroxides, oxides, and the like, alone or in admixture.

Specific examples include palladium oxide, palladium chloride, palladium nitrate, palladium acetate, palladium carbonate, palladium hydroxide, palladium oxylate, ruthenium oxide, ruthenium chloride, ruthenium nitrate, ruthenium acetate, ruthenium carbonate, ruthenium hydroxide, or any of the equivalent rhodium salts without needlessly lengthening the list.

The amount of catalyst employed in the hydrogenation process itself, the total hydrogenation catalysts excluding support, if any, can vary widely, but presently preferred and considered exemplary is a range of about 0.075 up to 1.75 percent by weight of palladium, and 0.15 up to 1.75 percent by weight of ruthenium or rhodium or both, based on weight of arylalkylenedinitrile charged.

Where a support is employed, the support is excluded from the weight ratios described above. Suitable supports not deleteriously affecting the catalystic hydrogenation processes described include carbon, kieselguhr, silica, alumina, silica-alumina, calcium carbonate, barium carbonate, asbestos, pumice, clays, and other well known inert catalytic support materials, alone, or in admixture. Rhodium component, or ruthenium component, and a palladium component, can be added to the catalyst support by any method well known in the art, such as dry mixing, impregnating from a solution or dispersion, or the like.

A presently preferred catalyst is a 70/30 mixture of ruthenium on alumina (5% Ru) and palladium on alumina (5% Pd).

In this hydrogenation process, it is preferred to employ a diluent. The diluent can be water, or tertiary alcohol such as those of 4 to 12 carbon atoms per molecule, or a mixture, presently preferring a water content of about 10 to 20 weight percent based on total of alcohol plus water. Exemplary of such alcohol diluents, are 2-methyl-2-propanol, 2-ethyl-2-butanol, 3-ethyl-3-hexanol, 2,4-dimethyl-2-pentanol, 2,3-dimethyl-3-pentanol, 3-ethyl-3-pentanol, 3,7-dimethyl-3-octanol, and the like, and mixtures thereof. To facilitate handling of the reaction mixtures, the weight ratio of unsaturated dinitrile reactants to diluent charged to the reaction zone is generally within the weight ratio range of about 0.01:100 to about 10:100.

Ammonia should be employed in the reduction process as a means of suppressing undesirable side reactions such as the formation of secondary and tertiary amines. Any amount of ammonia can be employed which is effective in deterring or reducing undesirable side reactions. Typically, the mole ratio of ammonia to cyano group, there being two cyano groups in each unsaturated dinitrile, is in the range of about 1:1 to about 25:1, and presently preferably is in the range of about 7:1 to about 15:1.

Any catalytic hydrogenation temperature can be employed which provides the desired degree of catalytic efficiency in the hydrogenation of aralkylenedinitrile containing feedstock. The hydrogenation temperatures generally will be within the range of about 130° C. to 250° C.

The catalytic hydrogenation of aralkylenedinitriles can be carried out at any hydrogen pressure wherein both the ring unsaturation and the nitrile groups are reduced in the presence of ammonia, hydrogen and a suitable diluent. Generally, suitable hydrogen pressures are within the range of about 1,000 to 3,000 psig, but lower or even higher hydrogen pressures can be employed where desired.

Recovery of the end product, the cycloalkylalkylenediamines, can be carried out by any conventional separation means. In general, at the conclusion of the catalytic hydrogenation process, the reaction effluent is cooled and depressurized with the recovery, if desired, of any ammonia or diluent which is vented from the reaction effluent during the depressurization operation. The ammonia or diluent can be returned or recycled to the hydrogenation zone if desired. The reaction products can be separated from the catalyst by conventional filtration means. The filtrate containing the at least substantially completely saturated diamines can be conveniently separated from any reaction byproducts or any diluent remaining in the filtrate by a conventional fractional distillation.

POLYAMIDES

The novel diamines, aralkylenediamines, or cycloalkylalkylenediamines, or both prepared according to our invention, can be reacted either or both, with polycarboxylic acids, such as di- or tricarboxylic acids, or both, to form novel polyamides.

Suitable dicarboxylic acids include the straight or branched chaim alpha, omega-dicarboxylic acids, such as those of $C_6$ to $C_{16}$ carbon atom content per molecule, preferably hydrocarbon dicarboxylic acids, with a presently preferred range of $C_8$ to $C_{12}$, for production of polyamides particularly suited to molding and fiber purposes. Exemplary dicarboxylic acids include terephthalic acid, adipic acid, sebacic acid, isophthalic acid, cyclohexane-1,4-dicarboxylic acid, and the like. Tricarboxylic acids of a similar carbon atom content and type, such as benzene tricarboxylic acid, also can be employed in minor amount in conjunction with the dicarboxylic acids, if desired, for special fiber properties.

Reaction conditions for preparation of polyamides by combination of one or more polycarboxylic acids and one or more of our novel diamines include heating of the reaction mixture, preferably in an inert atmosphere such as nitrogen atmosphere, using either stirred or unstirred reactors, under pressures of about 10 to 600 psig, at temperatures of such as about 200° to 300° C., over a time suitable for reaction to occur as between 1 and 3 hours. The reaction mixture preferably is maintained at about the maximum temperature reached over a further interval of such as 0.5 to several hours, frequently such as about 2 hours, if desired, for improved properties.

To recover the polymeric product, gaseous products from the reactor can be vented, and the mixture maintained under an inert atmosphere at a pressure of such as 1 atmosphere to very low vacuum for an additional interval to further remove gaseous products. In order to avoid crosslinking, it is preferred that about a 2 mole percent excess diamine be employed relative to the amount of the polycarboxylic acid.

EXAMPLES

The following examples are included in order to assist the understanding of our invention and to further illustrate various aspects. Particular reactants and particular conditions employed are intended to be illustrative and not limitative of the reasonable scope of our invention.

EXAMPLE I

A monoadduct reaction product comprising 5-methyl-5-hexenenitrile was prepared by the reaction of acrylonitrile and isobutylene in accordance with the following procedure: 40 g acrylonitrile containing 0.1 weight percent hydroquinone as polymerization inhibitor, 80 g diphenylamine and 200 g benzene were charged to a 1-liter stainless steel autoclave. The autoclave was closed, purged of air with nitrogen and 210 g isobutylene were added. This mixture was stirred for 3 hours while heating and maintained at 270° C. Subsequent gas-liquid chromatographic GLC analysis of the total product mixture indicated 95 percent conversion of the acrylonitrile. The reaction product mixture was concentrated on a rotary evaporator to afford 183 g of product residue. GLC analysis of the residue indicated 55.3 g 5-methyl-5-hexenenitrile, which represented 70.8 percent ultimate yield, and 3.5 g 2,4-dimethyl-4-pentenenitrile, which represented a 4.95 percent ultimate yield, which products together represented a monoadduct reaction product ultimate yield of 75.8 percent.

A diadduct reaction product comprising 5-methylenenonanedinitrile was prepared according to the following procedure: 80 g acrylonitrile containing 0.1 weight percent hydroquinone, 20 g triphenylphosphine, 168 g monoadduct reaction product prepared in accordance with the procedure set out above and 100 g benzene were charged to a 1-liter stainless steel autoclave. The autoclave was closed, purged of air with nitrogen, and pressurized to approximately 500 psig nitrogen. The mixture was stirred for approximately 5 hours while maintained at about 240° C. and at approximately 2000 psig. The reaction product mixture then was cooled, the autoclave vented, the solvent removed on a rotary evaporator, and the residue distilled through a Helipak column to yield the diadduct isomeric dinitrile product mixture. The results of GLC analysis determined a 63.3 percent conversion of acrylonitrile, a 42.3 percent ultimate yield of 5-methylenenonanedinitrile and a 3.4 percent ultimate yield of isomers thereof, which represents a diadduct reaction product ultimate yield of 45.7 percent. The isomers obtained comprise 5-methyl-4-nonenedinitrile, 2-methyl-4-methyleneoctanedinitrile, 2,4-dimethyl-3-octenedinitrile, 2,6-dimethyl-4-methyleneheptanedinitrile, and others.

The unsaturated dinitrile isomeric mixture from above was employed in an alkylation reaction according to our invention employing benzene as the aromatic compound and aluminum chloride as the Lewis acid catalyst.

To a reaction container equipped with reflux condenser, stirring means and temperature recording means, were added 0.556 mole 90 g of diadduct isomeric dinitrile from the above, and 13.5 mol 1200 ml of benzene. This admixture was stirred, and 1.5 mole 200 g of aluminum chloride AlCl₃ were added in small portions over an interval of approximately 1 hour. The admixture containing the Lewis acid was stirred while heated to and maintained at approximately 80° C. for 2 hours. Thereafter, the admixture was cooled, poured into an ice/water mixture, and the hydrolyzed mixture extracted with benzene. The benzene extract was washed with water, dried over anhydrous MgSO₄, and concentrated on a rotary evaporator.

A similar alkylation run was repeated as described above, employing 0.65 mole 105 g diadduct, 16.9 mole 1500 ml benzene, and 1.8 mole 240 g aluminum chloride, otherwise employing the same reaction conditions.

The products from the above two alkylation runs were combined and distilled through a short column to recover 254 grams of product for an overall 88 mole percent yield of aralkylenedinitrile based on the starting dinitrile.

The reaction product predominantly 5-phenyl-5-methylnonanedinitrile, was identified by infrared spectral analysis, nuclear magnetic resonance NMR spectra, elemental analysis and gas-liquid chromatography GLC analysis.

This example illustrates the production of the novel aryl-substituted dinitriles according to our invention in good yield.

EXAMPLE II

The aralkylenedinitrile, prepared as described in Example I above, was subjected to hydrogenation. In an autoclave were placed 3.95 mole 350 ml benzene, 10 g Raney nickel, and 0.28 mole 67 g 5-phenyl-5-methylnonanedinitrile. The system was flushed with nitrogen, charged with 7.1 mole 120 g of ammonia, and pressurized to 1200 psig with hydrogen. This admixture then was heated to and maintained at approximately 130° C. for about 2 hours. Thereafter, the system was depressurized, the admixture filtered, and then concentrated in a rotary evaporator.

A second hydrogenation run was made employing the same general reaction conditions, employing including 3.95 mole 350 ml benzene, 10 g Raney nickel, and 0.29 mole 70 g 5-phenyl-5-methylnonanedinitrile, and 120 g ammonia.

A third hydrogenation run was made employing 3.95 mole 350 ml benzene, 10 g Raney nickel, 0.44 mole 105 g 5-phenyl-5-methylnonanedinitrile, and 150 g ammonia. General conditions and operations were closely similar, except that pressurization of about 1400 psig with the hydrogen was maintained.

The products obtained from the described three runs were combined and fractionally distilled. A recovery of 232 g of product was made for a yield of 93 mole percent based on the starting phenyl-substituted dinitrile. The product recovered was identified by infrared analysis, elemental analysis, NMR, and GLC to be 5-phenyl-5-methyl-1,9-nonanediamine. However, infrared analysis indicated that the diamine product still contained a small amount of unreduced —C≡N. Therefore, the center cut from the fractional distillation was subjected to a further hydrogenation treatment. In an autoclave were placed 8.63 mole 350 ml methanol, 10 g Raney nickel, 142 g of the diamine product. The autoclave was flushed with nitrogen, and charged with 9.43 mole 160 g ammonia NH₃. This system was pressurized to 1500 psig with hydrogen, and heated to approximately 130° C. and maintained at this temperature for about 2 hours. The system then was depressurized, cooled, the product recovered by filtration of the reaction mixture and evaporation of diluent.

Another rehydrogenation run was made employing similar conditions with 82 g of the two heavier cuts of the product of Example II and 8.83 mole 150 g of ammonia. The product was recovered as described above.

The products from the above two runs were combined and fractionally distilled at reduced pressure of 1 millimeter mercury. Total product recovery of highly purified diamine was 176 g representing a 79 percent yield based on impure diamine. Analysis by GLC and infrared indicated complete reduction to 5-phenyl-5-methyl-1,9-nonanediamine.

The above runs further illustrate the preparation of the novel aralkylenediamines of our invention in good yield.

EXAMPLE III

A portion of the aralkylenediamine product comprising 5-phenyl-5-methyl-1,9-nonanediamine prepared as described in Example III above was employed in preparation of a polyamide. Aralkylenediamine comprising 5-phenyl-5-methyl-1,9-nonanediamine 20 millimoles 4.97 g was reacted with 20 millimoles 3.32 g of terephthalic acid and 0.46 mole 8.2 g water according to procedures generally employed in condensation polymerization processes for the preparation of polyamides from diamines and diacids.

The reactants were heated for about 1 hour in a glass vessel to raise the temperature from 120° to 210° C., were maintained at this temperature for approximately 3 hours, and then the temperature was raised to 290° C. over an interval of one-half hour and maintained at this latter temperature for an additional one-half hour with the reactor vented to maintain a pressure of between 15 and 20 psig, and maintained an additional hour at 290° C. with a nitrogen flush. The final one-half hour of reaction was at 290° C. at a low pressure of 30 millimeters mercury maintained by vacuum pump. The reaction mass was then allowed to cool to room temperature under nitrogen.

The polymeric product so obtained was recovered by breaking the glass vessel away from the solidified mass of polymer. The recovered polymer weighed 7.57 g and was white in appearance. The polymer thus produced had an inherent viscosity of 1.93 was determined in m-cresol at 30° C. at a concentration of 0.5 g/deciliter. The polymer melting temperature was 230° C. and the glass transition temperature was 130° C.

The above run illustrates the preparation of a polyamide using the novel aralkylenediamines of our invention.

EXAMPLE IV

A reactor equipped with stirring means, reflux condenser and thermometer was charged with 13.5 mole 1200 ml benzene and 0.65 mole 105 g of diadduct which was described in Example I. This mixture was stirred while 1.8 mole 240 g of $AlCl_3$ was added in small portions over a 30-minute period. After the $AlCl_3$ addition was complete the mixture was stirred for two hours at 80° C. The reaction mixture was then treated with ice water and extracted with benzene. The extract was dried over anhydrous $MgSO_4$, filtered, and concentrated by distilling away a major portion of the benzene. Five additional runs were made under the same conditions and the concentrated products combined and fractionally distilled under vacuum to give a total of 776 g of 5-phenyl-5-methylnonanedinitrile for an 83 mole percent yield based on the starting dinitrile diadduct.

An autoclave was charged with 0.42 mole 100 g 5-phenyl-5-methylnonanedinitrile, 10 g Raney nickel, and 9.86 mole 400 ml methanol. The reaction mixture was flushed with nitrogen and then charged with 8.9 mole 150 g ammonia. The reactor was then pressurized to 1500 psig with hydrogen and heated at 125° C. for two hours. The reactor was cooled, vented and the controls filtered and the filtrate concentrated in a rotary evaporator. Another hydrogenation run was made under essentially the same conditions described above except that 0.46 mole 110 g of 5-phenyl-5-methylnonanedinitrile was employed. The product of this run was concentrated as described above. Analysis of these concentrates by NMR and GLC indicated that complete hydrogenation of the nitrile groups to amino groups had been accomplished. The concentrates were then fractionally distilled under vacuum to give 180 g of 5-phenyl-5-methyl-1,9-nonanediamine for an 84 mole percent yielf based on the 5-phenyl-5-methylnonanedinitrile.

EXAMPLE V

A one liter autoclave was charged with 50 g 0.21 mole of a dinitrile consisting essentially of 5-phenyl-5-methylnonanedinitrile. Also charged to the reactor was 300 ml 237 g t-butyl alcohol, 25 ml water, 5 g of 5 percent by weight ruthenium on alumina and 2 g of 5 percent by weight palladium on alumina. The reactor was flushed with nitrogen and charged with 70 g 4.1 mole of ammonia. The reactor was pressured to 1200 psig with hydrogen and heated with stirring at 170° C. for two hours. Hydrogen uptake indicated only reduction of nitrile groups to amino groups had taken place thus producing the aralkylenediamine, 5-phenyl-5-methyl-1,9-nonanediamine.

A one liter autoclave was charged with 60 g 0.25 mole of a dinitrile consisting essentially of 5-phenyl-5-methylnonanedinitrile. Also charged to the reactor was 400 ml 316 g t-butyl alcohol and 5 g of 5 percent by weight ruthenium on alumina. The reactor was flushed with nitrogen and charged with 80 g 4.7 mole ammonia and pressured to 1200 psig with hydrogen. The reactor was heated at 170° C. for two hours with stirring. The reaction mixture was filtered and after the reactor was cooled and vented and the filtrate was concentrated by evaporation of the diluent. As in the first run, hydrogen uptake again indicated only reduction of the nitrile groups had occurred. The above run was repeated to provide more product for the hydrogenation of the aralkylenediamine to the cycloalkylenediamine.

The combined products prepared above, a mixture of aralkylenediamines consisting essentially of 5-phenyl-5-methyl-1,9-nonanediamine, totaling about 180 g of aralkylenediamines, was charged to a one liter autoclave. Also charged to the reactor was 500 ml 394 g t-butyl alcohol and 5 g of ruthenium dioxide $RuO_2$. The autoclave was flushed with nitrogen, pressured to 1,500 psig with hydrogen and heated at 140° C. for two hours stirring. No hydrogen uptake was observed and infrared analysis indicated essentially no reduction of the phenyl group had taken place. The unreacted diamine about 180 g was recovered by cooling and venting the reactor, filtering off the catalyst, and evaporating the diluent.

A 500 ml Parr hydrogenation reactor was charged with 200 ml 210 g, 3.5 mole glacial acetic acid and 2 g of platinum oxide. The catalyst was reduced with hydrogen and the reactor then charged with a mixture of 90 g 0.36 mole of the diamine product from above which consisted essentially of 5-phenyl-5-methyl-1,9-nonanediamine, and 100 ml 105 g, 1.75 mole of acetic acid. The reactor was pressured to 50 psig with hydrogen and the mixture agitated at about 25° C. for two hours. No sign of hydrogen uptake was observed so the temperature was raised to about 60° C. and the mixture agitated for an additional two hours with hydrogen uptake observed. The reaction mixture was neutralized, concentrated by evaporation of diluent and then fractionally distilled to give 72 g 0.28 mole of a cycloalkylalkylenediamine consisting essentially of 5-cyclohexyl-5-methyl-1,9-nonanediamine which boiled at 141°–146° C. at 0.1 mm Hg pressure.

The above data illustrate preparation of a novel cycloalkylalkylenediamine of our invention.

EXAMPLE VI

In this example are runs wherein polyamides were prepared from several different diacids utilizing diamines comprising essentially 5-cyclohexyl-5-methyl-1,9-nonanediamine, the last were obtained by the one-step hydrogenation of 5-methyl-5-phenylnonanedinitrile. The one-step hydrogenation was according to the following procedure.

A one-liter autoclave was charged with 30 g 0.125 mole of a dinitrile consisting essentially of 5-phenyl-5-methylnonanedinitrile, 5 g of 5 percent by weight ruthenium on alumina, 2 g of 5 percent by weight percent palladium on alumina, 400 ml 316 g of tert-butyl alcohol and 50 ml of water. The system was flushed with nitrogen, charged with 30 g 1.76 mole ammonia and pressured to 1500 psig with hydrogen.

The mixture was heated at 170° C. for two hours. Hydrogen uptake was essentially complete in about one hour. The reactor was cooled, vented and the contents filtered. The filtrate was analyzed by GLC which indicated complete hydrogenation. The filtrate 30 g was fractionally distilled to give 19 g 0.074 mole of the product consisting essentially of 5-cyclohexyl-5-methyl-1,9-nonanediamine for a yield of 63 percent by weight based on the filtrate charged to the distillation flask. The distillation residue weighed 9.5 g.

The so prepared 5-cyclohexyl-5-methyl-1,9-nonanediamine then was employed in the preparation of polyamides. Reactants were weighed into a glass reaction flask and the reactor pressurized with nitrogen, then evacuated. This nitrogen purge step was repeated twice more and the reaction vessel then immersed into a molten metal heating bath at 120° C. and the temperature gradually raised to 290°–320° C. over a 2.5 hour period. The temperature was held at 290°–320° C. for one hour then a nitrogen stream was passed through the flask for another one hour period at 290°–320° C. Finally, the reaction mixture was held under 20 mm Hg vacuum at 290°–320° C. for a one hour period. The reaction flask was then cooled to room temperature and broken to recover the solidified polymer therefrom.

Results are as reported below.

TABLE I

| Run No. | Diacid mmole | Diamine (a), mmole | Water, mmole | Polyamide (g) | M.P.,° C. | Tg,° C. |
|---|---|---|---|---|---|---|
| 1 | (b) 20 | 20 | 0 | 0.78 | 117 | 50 |
| 2 | (c) 20 | 20 | 0 | 0.61 | 138 | 52 |
| 3 | (d) 20 | 20 | 0 | 0.85 | 127 | 59 |
| 4 | (e) 20 | 21.4 | 96 | 0.54 | 180 | 138 |

TABLE I-continued

| Run No. | Diacid mmole | Diamine (a), mmole | Water, mmole | Polyamide (g) | M.P.,° C. | Tg,° C. |
|---|---|---|---|---|---|---|
| 5 | (e) 20 | 20 | 95 | 0.41 | 190 | 137 |
| 6 | (e) 20 | 20.6 | 94 | 0.75 | —(f) | 141 |

(a) Comprising essentially 5-cyclohexyl-5-methyl-1,9-nonanediamine.
(b) 1,12-Dodecanedioic acid
(c) Adipic acid
(d) Azelaic acid
(e) Terephthalic acid
(f) Not determined
(g) Inherent viscosity determined in m-cresol at 30° C. at a concentration of 0.25 g per 50 ml.

The above runs thus demonstrate the production of several polyamides employing a diamine comprising essentially 5-cyclohexyl-5-methyl-1,9-nonanediamine as one of the monomeric materials.

The novel dinitriles of our invention are useful in the preparation of aralkylenediamines, which are useful in the preparation of polyamides. Aralkylenediamines can be utilized for the preparation of cycloalkylalkylenediamines which are useful in the preparation of polyamides. The polyamides have utility as molding resins for the preparation of machine parts, tools, pipes, containers, or the like, in making bristles for the various types of brushes, as well as various other applications.

The disclosure, including data, illustrate the value and effectiveness of our invention. The examples, the knowledge and background of the filed of the invention and general principles of chemistry and other applicable sciences, have formed the bases from which the broad descriptions of the invention including the ranges of conditions and generic groups of operant components have been developed, which, in turn, have formed the bases for our claims here appended.

We claim:

1. As compositions of matter, aralkylenediamines represented by:

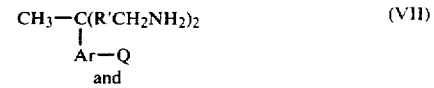
(VII)

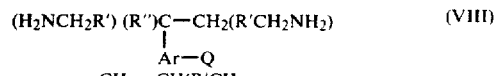
(VIII)

(IX)

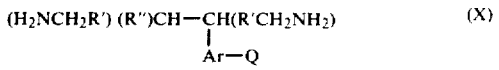
(X)

wherein each R' is an alkylene or alkylidene radical of at least one carbon atom, R" is an alkyl radical of at least one carbon atom, and Ar is a divalent phenylene or naphthylene radical wherein Q represents hydrogen or other substituent on said Ar, and wherein said —Ar—Q contains 6 to 22 carbon atoms, and wherein Q is selected from the group consisting of —H, —X, —R''', —N(R''')$_2$, —NH$_2$'HX, —OR''', —SH, —OH, and —SR''', wherein X is a halogen and is fluorine, chlorine, bromine, or iodine, and R''' is an alkyl radical of 1 to 6 carbon atoms.

2. The aralkylenediamines according to claim 1 wherein said R" contains 1 to 20 carbon atoms, and R''' contains 1 to 10 carbon atoms.

3. The aralkylenediamines according to claim 2 wherein said —Ar—Q is phenyl, and said aralkylenediamines contain 15 to 21 carbon atoms per molecule.

4. The aralkylenediamines according to claim 3 wherein said aralkylenediamine is 5-phenyl-5-methyl-1,9-nonanediamine.

5. As compositions of matter, aralkylenediamines as defined by claim 16 prepared by hydrogenating one or more aralkylenedinitriles represented by the formula:

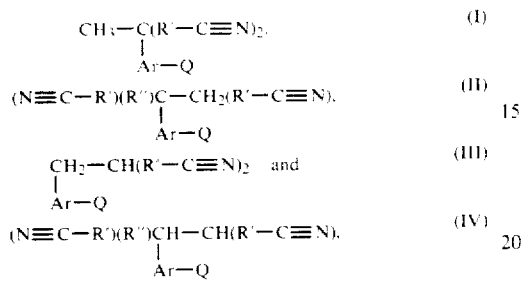

under hydrogenation conditions including the presence of hydrogen and ammonia sufficient to effectuate reduction of the —C≡N groups substantially without reduction of double bonds in said aralkylenedinitriles.

6. The aralkylenediamines according to claim 5 wherein said hydrogenation conditions include elevated pressures of about 500 to 5000 psig, at least one mole of ammonia per —C≡N group in said dinitriles, and employment of a cobalt, nickel, ruthenium, or rhodium based hydrogenation catalyst.

7. The aralkylenediamines according to claim 6 wherein said hydrogenation conditions are selected from a combination of ruthenium based catalysts at a reaction temperature of about 100°–250° C., rhodium based catalysts at a reaction temperature of about 25°–150° C., a cobalt base catalyst at a reaction temperature of about 70°–200° C., or a nickel base catalyst at a temperature of about 70°–200° C.

8. As compositions of matter, cycloalkylalkylenediamines represented by:

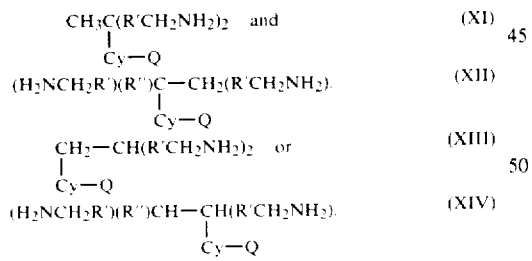

wherein each R' is a linear or branched alkylene or alkylidene radical of at least one carbon atom with one valence attached to the aminomethyl group as indicated by the formulae; R" is a linear or branched alkyl radical of at least one carbon atom; Cy represents a cyclohexylene or perhydronaphthylene radical and wherein Q represents hydrogen, —X, —R''', —N(R''')₂, —NH₂.HX, —OR''', —SH, —OH, or —SR''', wherein X is fluorine, chlorine, bromine, or iodine, and wherein R''' is an alkyl radical of 1 to 6 carbon atoms.

9. Cycloalkylalkylenediamines according to claim 8 wherein said —Cy—Q contains 6 to 20 carbon atoms, R' up to 20 carbon atoms, and R" up to 10 carbon atoms.

10. Cycloalkylalkylenediamines according to claim 9 wherein said —Cy—Q is the cyclohexyl radical with Q as hydrogen, and said cycloalkylalkylenediamine contain 15 to 21 carbon atoms per molecule.

11. Cycloalkylalkylenediamines according to claim 10 wherein said cycloalkylalkylenediamine is 5-cyclohexyl-5-methyl-1,9-nonanediamine.

12. The composition according to claim 8 wherein said composition comprises a mixture of said XI and XII.

13. As compositions of matter, cycloalkylalkylenediamines represented by one or more of the formulae:

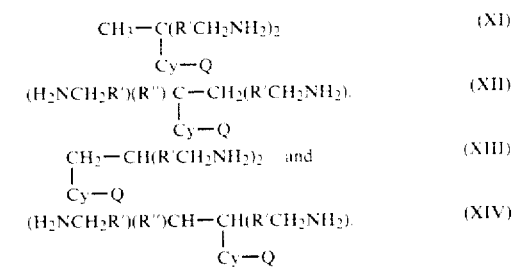

prepared by the process which comprises hydrogenating one or more aralkylenediamines represented by the formulae:

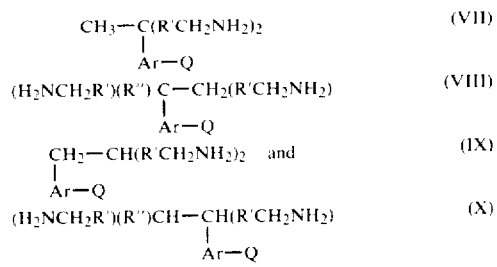

under hydrogenation conditions including the presence of hydrogen, and catalyst, effective to hydrogenate said Ar to said Cy, wherein each R' is a linear or branched alkylene or alkylidene radical of at least one carbon atom with one valence attached to the aminomethyl group as indicated by the formulae; R" is a linear or branched alkyl radical of at least one carbon atom; said Ar represents a phenylene or naphthylene radical wherein Q represents hydrogen, —X, —R''', —N(R''')₂, —NH₂.Hx, —OR''', —SH, —OH, or —SR''', wherein X is fluorine, chlorine, bromine, or iodine, and R''' is an alkyl radical of up to 6 carbon atoms, and wherein Cy represents a fully hydrogenated Ar.

14. The cycloalkylalkylenediamines according to claim 13 wherein said hydrogenation conditions include a temperature of about 25°–150° C., a hydrogen pressure of about 0 to 200 psig, and said catalyst is a platinum-based catalyst.

15. The cycloalkylalkylenediamines according to claim 14 wherein said aralkylenediamine comprises 5-phenyl-5-methyl-1,9-nonanediamine, and the resulting cycloalkylalkylenediamine comprises 5-cyclohexyl-5-methyl-1,9-nonanediamine.

16. A process for preparing cycloalkylalkylenediamines which comprises hydrogenating under hydrogenation conditions at least one aralkylenedinitrile as defined by claim 1, under hydrogenation conditions sufficient to reduce —C≡N groups and said —Ar to —CH₂NH₂ groups and —Cy— groups respectively, wherein said resulting cycloalkylalkylenediamines can be represented by:

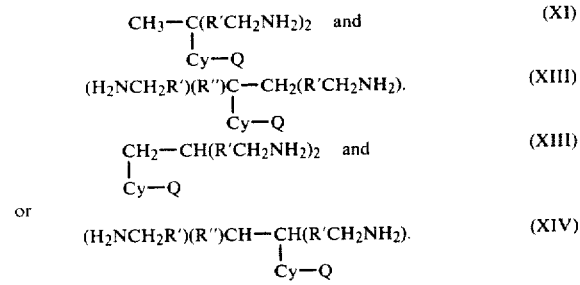

wherein Cy represents a saturated Ar group,
wherein said hydrogenation process is effectuated in a substantially one step operation employing a 2-component catalyst comprising a palladium component with at least one of ruthenium or rhodium component and including a ratio of about 0.1:1 to about 10:1 palladium to either or both of ruthenium and rhodium,
wherein said Q is —H, —X, —R‴, —N(R‴)₂, —NH₂.HX, —OR‴, —SH, —OH, —SR‴,
wherein X is halogen and is fluorine, chlorine, bromine, or iodine, and R' is an alkyl radical of up to 6 carbon atoms.

17. The cycloalkylalkylenediamines according to claim 16 wherein said hydrogenation is conducted in the presence of ammonia to the extent of about 1 mole of ammonia per —C≡N group present in said dinitrile, and said hydrogenation conditions include a reaction temperature in the range of about 130°–250° C. and a hydrogen pressure of about 1000 to 3000 psig.

18. The compositions according to claim 1 wherein said —Ar—Q is a monovalent radical derived from benzene, naphthalene, toluene, chlorobenzene, N,N-dimethylaniline, aniline hydrochloride, anisole, benzenethiol, 1-chloronapthalene, phenol, methylphenyl sulfide, 2-methoxynaphthalene.

19. The composition of matter of claim 1 wherein said aralkylenediamines contain 9 to 30 carbon atoms per molecule.

20. The composition of matter of claim 13 wherein said cycloalkylalkylenediamines contain 9 to 30 carbon atoms per molecule.

21. The composition of matter of claim 16 wherein said cycloalkylalkylenediamines contain 9 to 30 carbon atoms per molecule.

* * * * *